(12) United States Patent
Ha et al.

(10) Patent No.: US 8,787,332 B2
(45) Date of Patent: Jul. 22, 2014

(54) BIOLOGICAL SIGNAL SENSOR APPARATUS, WIRELESS SENSOR NETWORK, AND USER INTERFACE SYSTEM USING BIOLOGICAL SIGNAL SENSOR APPARATUS

(75) Inventors: Young-Guk Ha, Daejeon (KR); Joo Chan Sohn, Daejeon (KR); Kyung-Il Kim, Daejeon (KR); Hyeonsung Cho, Daejeon (KR); Young Cheol Go, Daejeon (KR); Hyun Kyu Cho, Daejeon (KR); Young-Jo Cho, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1265 days.

(21) Appl. No.: 12/630,723

(22) Filed: Dec. 3, 2009

(65) Prior Publication Data

US 2010/0160744 A1 Jun. 24, 2010

Related U.S. Application Data

(63) Continuation of application No. PCT/KR2008/001382, filed on Mar. 12, 2008.

(30) Foreign Application Priority Data

Jun. 4, 2007 (KR) .................. 10-2007-0054374
Oct. 11, 2007 (KR) .................. 10-2007-0102549

(51) Int. Cl.
*H04W 4/00* (2009.01)
*H04B 7/00* (2006.01)
*A61B 5/00* (2006.01)
*H04W 4/02* (2009.01)
*H04L 29/08* (2006.01)
*G08B 21/02* (2006.01)
*G08B 21/04* (2006.01)
*H04W 48/04* (2009.01)
*H04W 88/04* (2009.01)
*H04L 12/28* (2006.01)

(52) U.S. Cl.
CPC ............... *H04W 4/02* (2013.01); *H04W 48/04* (2013.01); *H04W 88/04* (2013.01); *H04L 12/2827* (2013.01); *H04L 67/12* (2013.01); *H04L 67/18* (2013.01); *G08B 21/0202* (2013.01); *G08B 21/0446* (2013.01); *A61B 5/0002* (2013.01)
USPC ............ 370/338; 370/328; 370/310; 600/301

(58) Field of Classification Search
None
See application file for complete search history.

(56) References Cited

U.S. PATENT DOCUMENTS

| | | | |
|---|---|---|---|
| 2002/0019584 A1* | 2/2002 | Schulze et al. ................ | 600/300 |
| 2004/0230638 A1* | 11/2004 | Balachandran et al. ....... | 709/200 |
| 2006/0088014 A1* | 4/2006 | Ganesh ......................... | 370/338 |
| 2006/0133320 A1* | 6/2006 | Kim et al. ...................... | 370/331 |
| 2006/0149905 A1* | 7/2006 | Park et al. ..................... | 711/141 |
| 2006/0178567 A1* | 8/2006 | Goh et al. ...................... | 600/300 |
| 2006/0229520 A1 | 10/2006 | Yamashita et al. | |
| 2006/0247505 A1* | 11/2006 | Siddiqui ........................ | 600/300 |
| 2007/0005292 A1 | 1/2007 | Jin | |
| 2007/0027922 A1* | 2/2007 | Mishina et al. ............. | 707/104.1 |
| 2007/0255111 A1* | 11/2007 | Baldus et al. ................. | 600/300 |
| 2008/0031139 A1* | 2/2008 | Muro et al. ................... | 370/237 |
| 2008/0076572 A1* | 3/2008 | Nguyen et al. ................. | 463/42 |
| 2008/0113785 A1* | 5/2008 | Alderucci et al. ............. | 463/29 |
| 2010/0008275 A1* | 1/2010 | Lee et al. ...................... | 370/311 |

FOREIGN PATENT DOCUMENTS

| | | |
|---|---|---|
| KR | 10-2002-0078327 A | 10/2002 |
| KR | 10-2003-0061157 A | 7/2003 |
| KR | 10-2005-0050350 A | 5/2005 |
| KR | 10-2006-0014837 A | 2/2006 |
| KR | 10-2006-0069147 A | 6/2006 |
| KR | 10-2006-0070165 A | 6/2006 |

OTHER PUBLICATIONS

International Search Report for PCT/KR2008/001382 filed Mar. 12, 2008.

* cited by examiner

Primary Examiner — Kevin C Harper
Assistant Examiner — Peter Chen

(57) ABSTRACT

A biological signal sensor apparatus worn on a user's body includes: a sensor unit for sensing physical states or movements of a user to generate biological signal data; a wireless communications unit for performing wireless data communications with a wireless sensor network to transmit the biological signal data; a sensor network protocol processing unit for processing protocols for end-to-end communications between the wireless communications unit and the wireless sensor network and for performing a mobility support procedure for the biological signal sensor apparatus; a processor for controlling the wireless data communications, the end-to-end communications, and the mobility support procedure to allow the biological signal sensor apparatus to serve as a mobile wireless sensor node; and a connection unit for connecting the sensor unit and the processor. The biological signal sensor apparatus serves as a mobile wireless sensor node in the wireless sensor network.

10 Claims, 14 Drawing Sheets

FIG. 6

| SENSOR NODE ID | SENSOR SPACE NAME | SENSOR COORDINATE |
|---|---|---|
| 0005 | INNER ROOM | 100,120 |
| 0012 | LIVING ROOM | 225,350 |
| ⋮ | ⋮ | ⋮ |
| 0007 | GARDEN | 300,135 |

FIG.9

| SENSOR NODE ID | WIRELESS SIGNAL STRENGTH | TIMESTAMP |
|---|---|---|
| 0005 | 250 | 12365 |
| 0012 | 130 | 10010 |
| ⋮ | ⋮ | ⋮ |
| 0007 | 132 | 12370 |

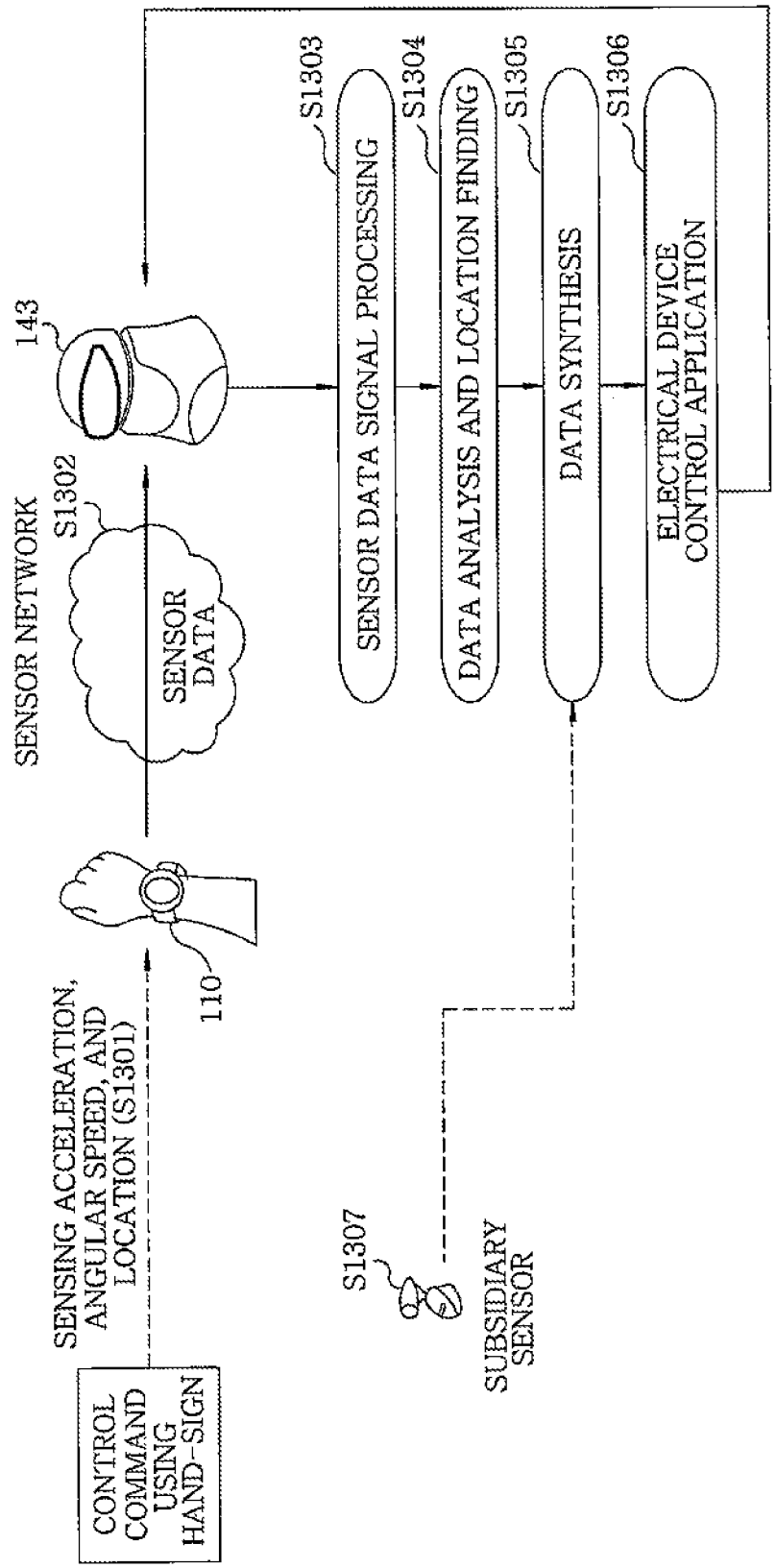

BIOLOGICAL SIGNAL SENSOR APPARATUS, WIRELESS SENSOR NETWORK, AND USER INTERFACE SYSTEM USING BIOLOGICAL SIGNAL SENSOR APPARATUS

This application is a Continuation Application of PCT International Application No. PCT/KR2008/001382 filed on 12 May 2008, which designated the United States.

FIELD OF THE INVENTION

The present invention relates to a biological signal sensor apparatus, a wireless sensor network, and a user interface system using the biological signal sensor apparatus; and, more particularly, a biological signal sensor apparatus for sensing biological signals of a user, a wireless sensor network, and a user interface system for providing application services based on location information.

BACKGROUND OF THE INVENTION

With the recent developed and widespread computer networking technology, ubiquitous computing technology and a wireless sensor network or a ubiquitous sensor network (USN) technology come into the spotlight as next-generation computing technologies.

The ubiquitous computing technology is directed to provision of all user-desired computing services anytime and anywhere and basically based on a wireless sensor network. To be specific, computers and sensors are installed at invisible positions in ambient living spaces and connected with each other over a wireless network, thereby sensing various data, recognizing contexts and situations based on the data, and providing a variety of services.

A ubiquitous healthcare system (u-healthcare system) is a killer application of the ubiquitous computing technology. The ubiquitous healthcare system results from combination of the ubiquitous computing technology and healthcare services which are a matter of primary concern nowadays, and facilitates checking and managing health states of children, aged or feeble people, chronic patients, and the like in real life anytime and anywhere. A currently developed ubiquitous healthcare system is configured with a wireless or wired body/wrist wearable biological signal sensor apparatus, which is connected to a portable user terminal or a computer and interoperates with a remote hospital or a healthcare server.

FIG. 1 illustrates a configuration of a conventional user interface system using a biological signal sensor apparatus wherein the system is a ubiquitous healthcare system using a wrist-wearable biological signal sensor apparatus.

As shown in FIG. 1, the conventional ubiquitous healthcare system includes a wrist-wearable biological signal sensor apparatus 10 for collecting health information of a user 1 while worn on a wrist of the user 1; and a portable terminal 30, a home server 40 and a personal computer (PC) 50 which are connected with the wrist-wearable biological signal sensor apparatus 10 via a wireless communications link 20.

The portable terminal 30, e.g., a personal digital assistant (PDA), is connected with a wireless local area network (LAN) access point 70 via a wireless LAN 60 which in turn is connected with a healthcare server 90 at a healthcare authority via the Internet 80. The home server and the PC 50, which can access the Internet 80 by themselves, are directly connected with the healthcare server 90.

In the above ubiquitous healthcare system, the wrist-wearable biological signal sensor apparatus 10 collects the health information of the user 1 on occasion, and, the collected health information is transmitted to the healthcare server 90 via the portable terminal 30, the home server 40 or the PC 50.

Drawbacks of the user interface system using a biological signal sensor apparatus, e.g., the ubiquitous healthcare system of FIG. 1, are as follows. First, it cannot support free mobility of a user due to a limited communicable distance of a wireless or wired communications link. Second, it cannot recognize at which space a user is currently located even though it can perform wireless communications in an actual use-environment having several spaces. These drawbacks are problems to be solved for implementing a real sense of ubiquitous healthcare system through which healthcare can be performed anytime and anywhere. In particular, provision of location information necessary for rescue of a user in an emergency such as a heart attack, a blackout, a trouble in movements and the like is a very important and essential function of the ubiquitous healthcare system.

The GPS (Global Positioning System) based location recognition technique is being applied to various fields as means for detecting location of a user. However, the GPS is inadequate for an ordinary life because it is not available in an indoor area.

Further, configuration and functions of the conventional wrist-wearable biological signal sensor apparatus are focused only on healthcare. Therefore, the conventional wrist-wearable biological signal sensor apparatus does not recognize behavioral and emotional states of a user which can be recognized using various biological signals sensed from the user, and thus, cannot be utilized as an interface with a variety of ubiquitous service devices.

SUMMARY OF THE INVENTION

In view of the above, the present invention provides a biological signal sensor apparatus for sensing biological signals of a user, a wireless sensor network, and a user interface system for providing application services based on location information of the user.

In accordance with a first aspect of the invention, there is provided a biological signal sensor apparatus worn on a user's body, including: a sensor unit for sensing physical states or movements of a user to generate biological signal data; a wireless communications unit for performing wireless data communications with a wireless sensor network to transmit the biological signal data; a sensor network protocol processing unit for processing protocols for end-to-end communications between the wireless communications unit and the wireless sensor network and for performing a mobility support procedure for the biological signal sensor apparatus; a processor for controlling the wireless data communications, the end-to-end communications, and the mobility support procedure to allow the biological signal sensor apparatus to serve as a mobile wireless sensor node; and a connection unit for connecting the sensor unit and the processor.

In accordance with a second aspect of the invention, there is provided a wireless sensor network, including: a biological signal sensor apparatus, worn on a user's body and serving as a mobile wireless sensor node, for sensing biological signals of a user to generate biological signal data; a plurality of stationary wireless sensor nodes, installed in living spaces of the user, for performing wireless communications with the biological signal sensor apparatus; and a plurality of wireless sink nodes wirelessly connected with the stationary wireless sensor nodes to form the wireless sensor network.

In accordance with a third aspect of the invention, there is provided a user interface system, including: a biological signal sensor apparatus, worn on a user's body and serving as a mobile wireless sensor node in a wireless sensor network, for sensing biological signals of a user to generate biological signal data; a plurality of stationary wireless sensor nodes, installed in living spaces of the user, for performing wireless communications with the biological signal sensor apparatus; a plurality of wireless sink nodes wirelessly connected with the stationary wireless sensor nodes to form the wireless sensor network; and a service unit for processing the biological signal data transmitted via the wireless sink nodes to provide to the user application services based on location information of the user who stays in any one of the living spaces in the wireless sensor network.

In accordance with the present invention, wide-area user mobility can be supported by using a sensor network having a biological signal sensor apparatus and inexpensive wireless sensor nodes installed at several positions in indoor/outdoor living spaces of a user. Further, a current location and behavioral states of the user can be recognized through interoperation between wireless sensor nodes installed at specific positions and a user-worn wireless sensor node. From this, the user interface system of the present invention can be used as a user interface not only for a ubiquitous healthcare service but also for various services requiring recognition of physical/emotional state changes, behaviors, and commands of a user. Therefore, a variety of ubiquitous application services such as game/education services, childcare services, and remote control services for intelligent service robots, computers or digital appliances can be effectively provided.

BRIEF DESCRIPTION OF THE DRAWINGS

The above features of the present invention will become apparent from the following description of embodiments, given in conjunction with the accompanying drawings, in which:

FIG. 6 illustrates a configuration of a sensor map database for use in the user interface system in accordance with the present invention;

FIG. 9 illustrates a configuration of an embodiment of a nearby node table for use in the mobility support procedure for a wireless sensor node in the user interface system in accordance with the present invention;

FIG. 14 illustrates an exemplary view of the user interface system using a biological signal sensor apparatus to provide an electrical device remote control service.

DETAILED DESCRIPTION OF THE EMBODIMENT

Hereinafter, embodiments of the present invention will be described in detail with reference to the accompanying drawings, which form a part hereof.

In this specification, the term "biological signals" is used to refer to signals detected from a user's body, and it includes physical states and movements of a user.

Figure 1:
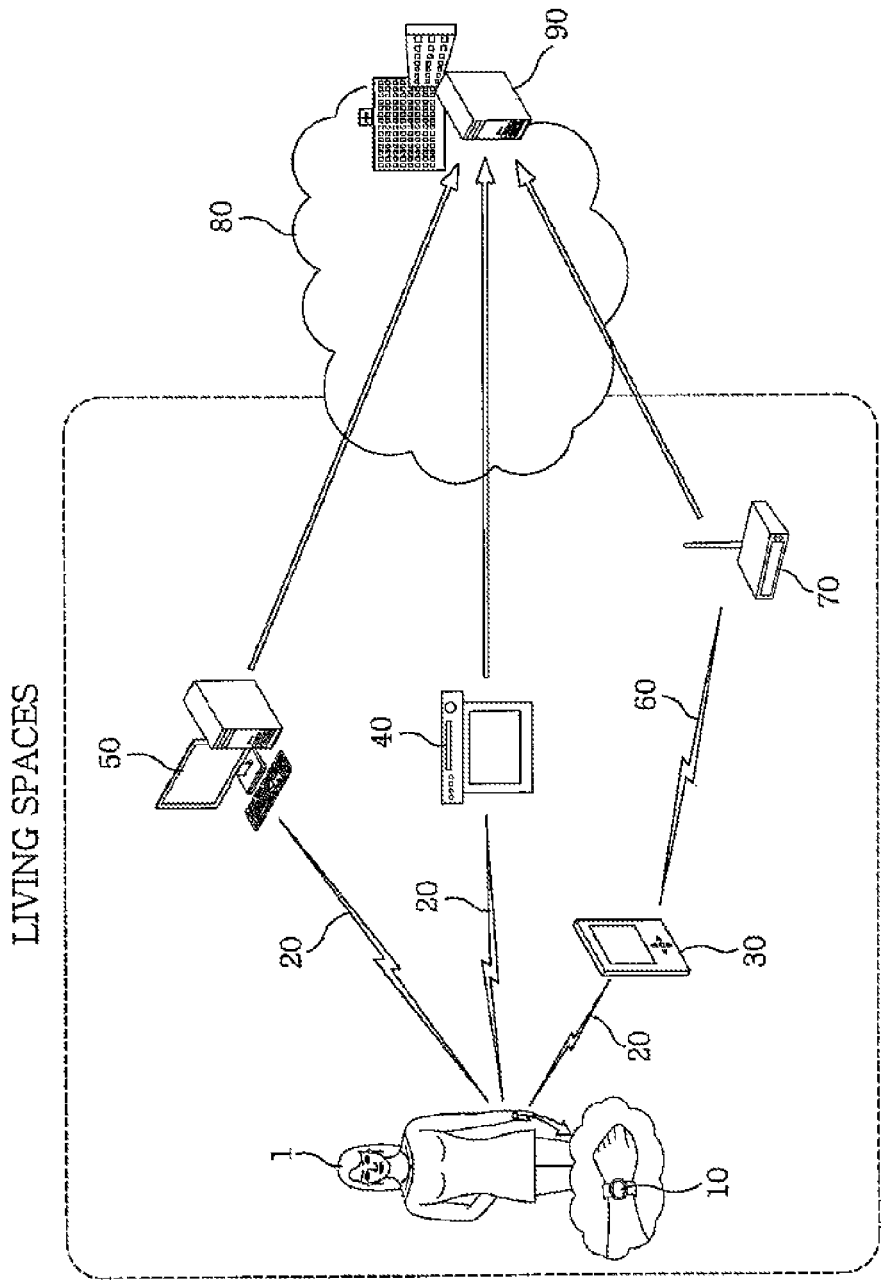
FIG. 1 illustrates a configuration of a conventional user interface system using a biological signal sensor apparatus wherein the system is a ubiquitous healthcare system.
Figure 2:
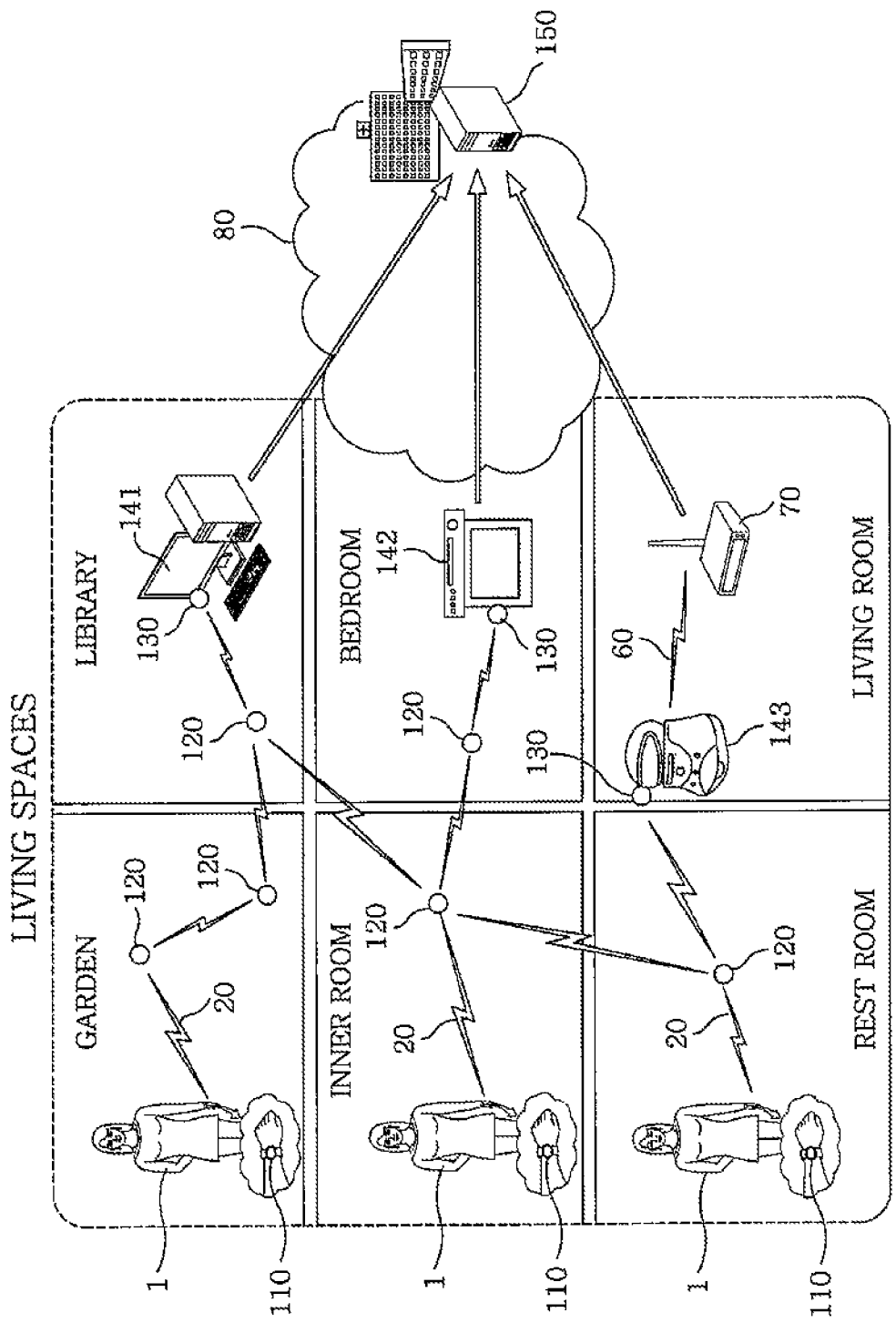
FIG. 2 illustrates a configuration of a user interface system using a biological signal sensor apparatus in accordance with the present invention.

FIG. 2 illustrates a configuration view of a user interface system using a biological signal sensor apparatus in accordance with the present invention.

As shown in FIG. 2, a user interface system in accordance with the present invention includes: a biological signal sensor apparatus 110, which serves as a mobile wireless sensor node, for sensing biological signals of a user 1 while worn on a wrist or the like of the user 1 to generate biological signal data based thereon; a plurality of stationary wireless sensor nodes 120, installed in living spaces of the user 1 such as a garden, a library, an inner room, a bedroom, a rest room, a living room and the like, for performing wireless communications with the biological signal sensor apparatus 110 via wireless communications links 20; a plurality of wireless sink nodes 130 connected with the stationary wireless sensor nodes 120 via the wireless communications links 20 to form a wireless sensor network; service apparatuses 141 to 143, connected with the wireless sink nodes 130, for processing the biological signal data generated by the biological signal sensor apparatus 110 and providing application services based on location information of the user 1 in the wireless sensor network; a service server 150, connected with the service apparatuses 141 to 143 via an external communications network such as the Internet 80, for providing the application services based on the biological signal data via the service apparatuses 141 to 143; and subsidiary sensors (not shown) for obtaining images of the user 1 to assist the biological signal sensor apparatus 110.

The service apparatuses 141 to 143 provide a variety of application services based on the biological signal data generated by the biological signal sensor apparatus 110. Each of the service apparatuses 141 to 143 may be implemented with: a personal computer accessible to the wireless sink nodes 130 and the Internet 80; a home server accessible to the wireless sink nodes 130 and the Internet and forming a home network; an intelligent robot accessible to the wireless sink nodes 130 and the Internet 80 via a wireless LAN 60 and a wireless LAN access point 70; or the like. Since the personal computer, the home server, and the intelligent robot have enough excellent processing powers to provide a variety of application services, each of them can be solely dedicated as the service apparatus 141, 142 or 143. Even if a service apparatus connected with the wireless sink node 130 has an insufficient processing power to provide the application services, the service apparatus can be used in conjunction with an additional host apparatus having an appropriate processing power. These service apparatus and host apparatus are an exemplary embodiment of a service unit to process biological signal data transmitted via the wireless sink node 130 and provide application services based on the location information of the user in a wireless sensor network.

Each of the stationary wireless sensor nodes 120 has an ID (identification) assigned thereto, and communicates with each other in a multi-hop fashion in which a communicable distance in end-to-end wireless communications is not limited. The biological signal sensor apparatus 110, which serves as a mobile wireless sensor node, performs a mobility support procedure (i.e., a handover procedure) while moving, in which the biological signal sensor apparatus 110 automatically creates a connection with the most nearby stationary wireless sensor node 120, so that seamless connection with the sensor network can be guaranteed.

A space (e.g., an inner room, a bedroom, a living room and the like) where the user stays at present is found by using the stationary wireless sensor node 120 currently connected with the biological signal sensor apparatus 110 as a location reference node.

Movements, biological information and location information of the user 1, which are collected by the biological signal sensor node 110 and the sensor network, are employed to provide services to the user 1 via application programs embedded in the service apparatuses 141 to 143. Or, they are transmitted to the service server 150 connected with the Internet 80 to provide more specialized services to the user 1. The service server 150 may be implemented with a CDSS (Clinical Decision Support System) in a medical authority.

Figure 3:
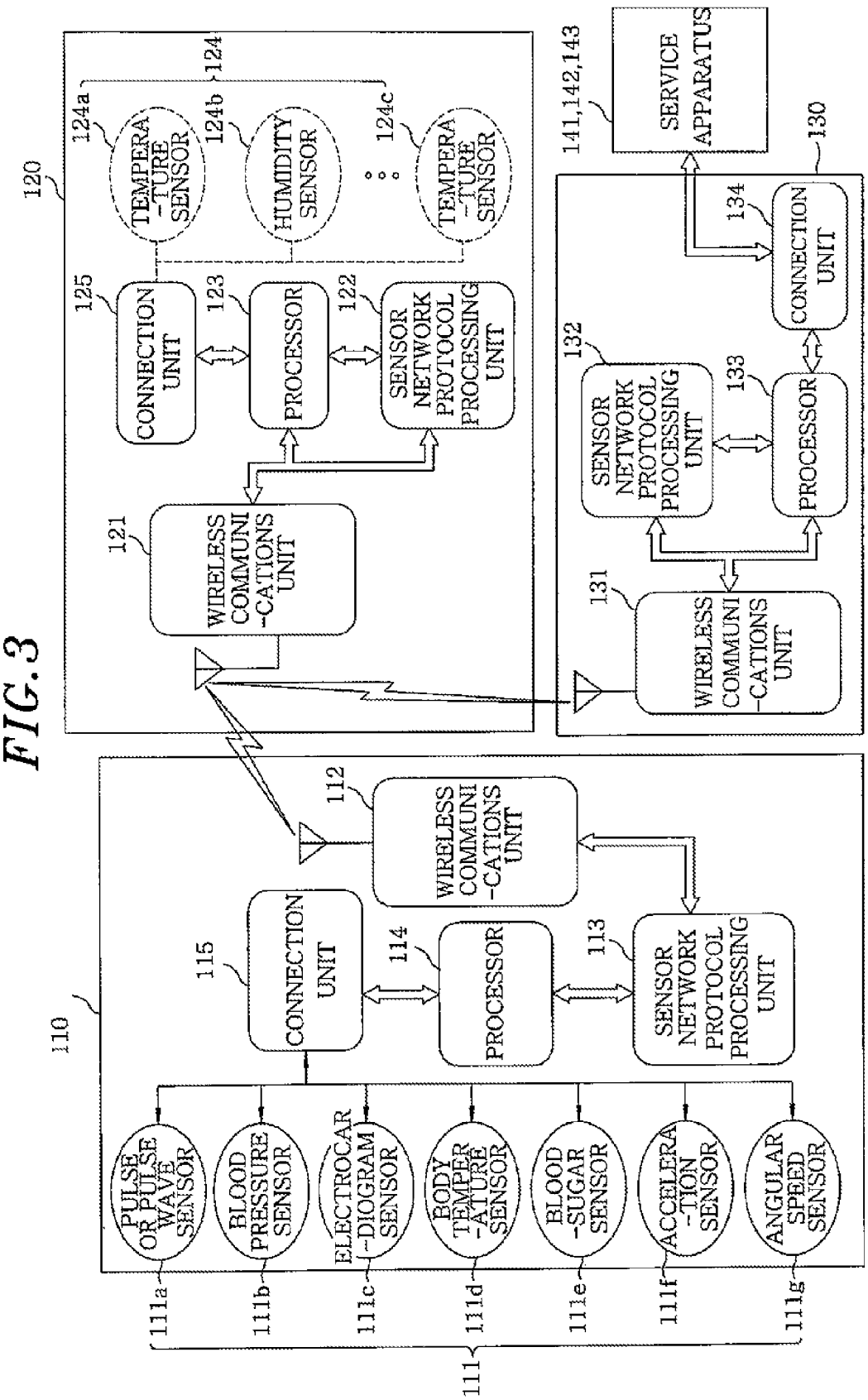
FIG. 3 illustrates a detailed configuration of a biological signal sensor apparatus, a stationary wireless sensor node, and a wireless sink node, which form the user interface system in accordance with the present invention.

FIG. 3 illustrates a detailed configuration of the biological signal sensor apparatus, the stationary wireless sensor node, and the wireless sink node as shown in FIG. 2, all of which form the user interface system in accordance with the present invention.

Referring to FIG. 3, the biological signal sensor apparatus 110 includes: a sensor unit 111 for sensing physical states and movements of the user 1 to generate biological signal data; a wireless communications unit 112 for wirelessly transmitting and receiving the biological signal data to and from the stationary wireless sensor node 120; a sensor network protocol processing unit 113 for performing end-to-end multi-hop communications between the wireless communications unit 112 and the stationary wireless sensor node 120 and processing protocols for the mobility support procedure; a processor 114 for controlling wireless data transmission and reception, the end-to-end multi-hop communications, and the mobility support procedure; and a connection unit 115 for connecting the sensor unit 111 and the processor 114. The sensor unit 111 has a pulse/pulse wave sensor 111*a*, a blood pressure sensor 111*b*, an electrocardiogram sensor 111*c*, a body temperature sensor 111*d*, a blood-sugar sensor 111*e*, an acceleration sensor 111*f*, and an angular speed sensor 111*g*. The sensor network protocol processing unit 113 may be implemented as independent hardware or firmware. The wireless communications unit 112 may be implemented by using a wireless communications standard using the license-free ISM (industrial, scientific, medical) radio bands, e.g., ZigBee (IEEE 802.15.4), Bluetooth, or the like. The biological signal sensor apparatus 110 may be made of a wrist-wearable type such as a wrist-band or a wrist-watch.

The stationary wireless sensor node 120 includes: a wireless communications unit 121 for wirelessly transmitting and receiving the biological signal data to and from the biological signal sensor apparatus 110 and the wireless sink node 130; a sensor network protocol processing unit 122 for performing end-to-end multi-hop communications between the wireless communications unit 121 and the biological signal sensor apparatus 110 and processing protocols for the mobility support procedure; a processor 123 for controlling wireless data transmission and reception, the end-to-end multi-hop communications, and the mobility support procedure; a sensor unit 124 for sensing a living environment of the user 1; and a connection unit 125 for connecting the sensor unit 124 and the processor 123. The sensor unit 124 has a temperature sensor 124*a*, a humidity sensor 124*b*, and an illuminance sensor 124*c*. The stationary wireless sensor node 120 can be implemented without the sensors 124*a* to 124*c* and the connection unit 125 if the living environment of the user 1 needs not to be sensed. The stationary wireless sensor node 120 can be easily attached to the living spaces.

The wireless sink node 130 includes: a wireless communications unit 131 for wirelessly transmitting and receiving the biological signal data to and from the stationary wireless sensor node 120; a sensor network protocol processing unit 132 for performing end-to-end multi-hop communications between the wireless communications unit 131 and the stationary wireless sensor node 120; a processor 133 for controlling wireless data transmission and reception and the end-to-end multi-hop communications; and a connection unit 134 for connecting the processor 133 and the service apparatuses 141 to 143. The connection unit 134 may use serial communications such as RS-232C, USB (Universal Serial Bus), and the like.

Figure 4:
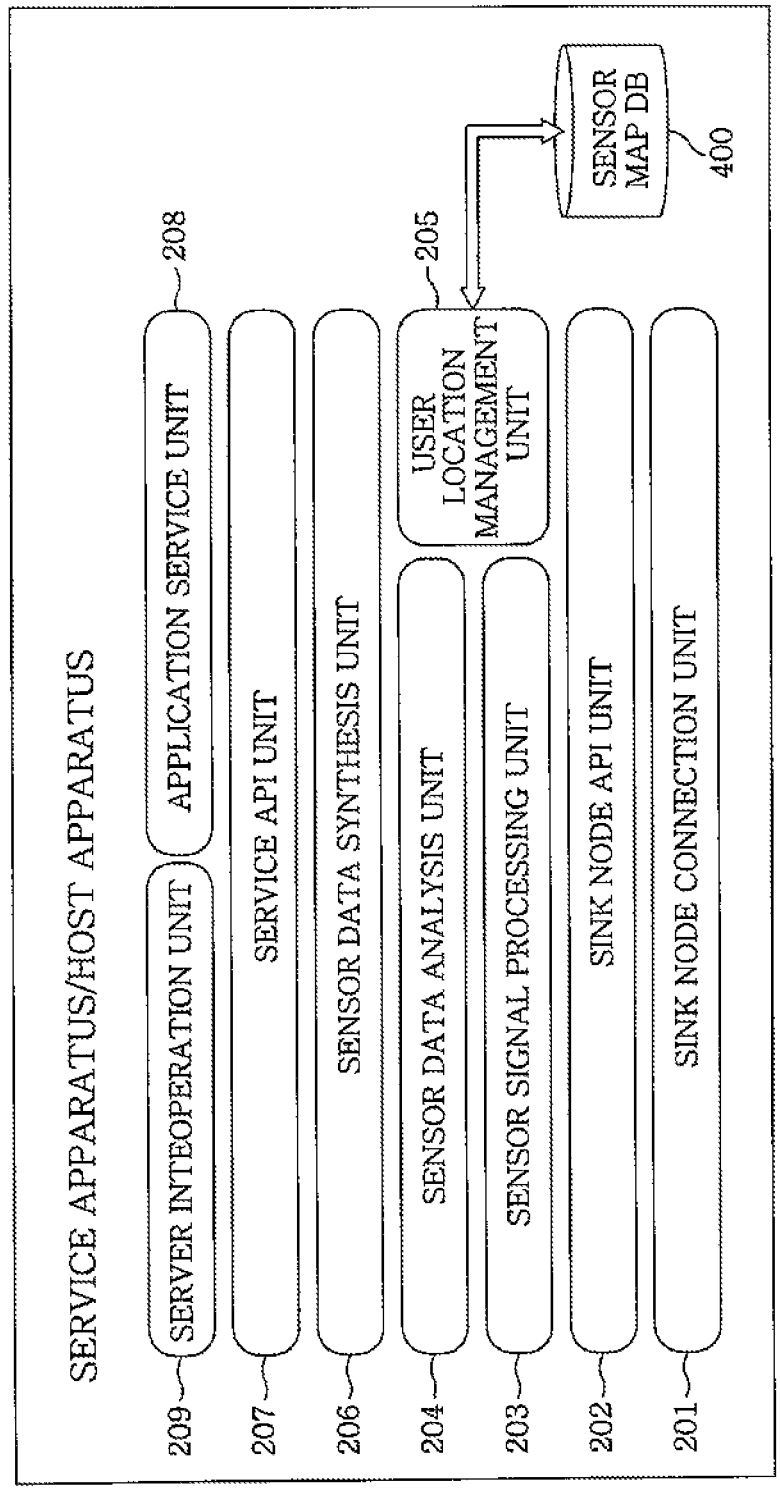
FIG. 4 illustrates a detailed configuration of a service apparatus in accordance with the present invention.

FIG. 4 illustrates a detailed configuration view of a service apparatus shown in FIG. 2.

Referring to FIG. 4, each of the service apparatuses 141 to 143 includes: a sink node connection unit 201 for providing a connection with the wireless sink node 130; a sink node application program interface (API) unit 202 for providing basic libraries to support communications with the wireless sink node 130; a sensor signal processing unit 203 for performing pre-processing, such as filtering, conversion, and the like, on the biological signal data received from the wireless sink node 130; and a sensor data analysis unit 204 for analyzing patterns of the pre-processed biological signal data by applying learning/recognizing algorithm such as a Hidden Markov Model (HMM), a neural network, and the like.

Each of the service apparatuses 141 to 143 further includes: a user location management unit 205 for retrieving a current location information of the user 1 from a sensor map database (DB) 400 based on a nearby sensor node ID included in the biological signal data transmitted by the wireless sink node 130; a sensor data synthesis unit 206 for extracting new meaningful context by combining the biological signal data analyzed by the sensor data analysis unit 204 and data obtained by a subsidiary sensor apparatus (not shown) to assist the biological signal sensor apparatus 110; a service API unit 207 for providing libraries for use in development of application service programs; an application service unit 208 for providing application services to the user 1 via the service apparatuses 141 to 143 based on the biological signal data analyzed by the sensor data analysis unit 204 or synthesized by the sensor data synthesis unit 206 and the location information of the user 1 retrieved by the user location management unit 205; and a server interoperation unit 209 for providing interoperability with the service server 150. Here, the nearby sensor node ID and the sensor map DB 400 will be described below with reference to FIG. 5 and FIG. 6, respectively.

Figure 5:
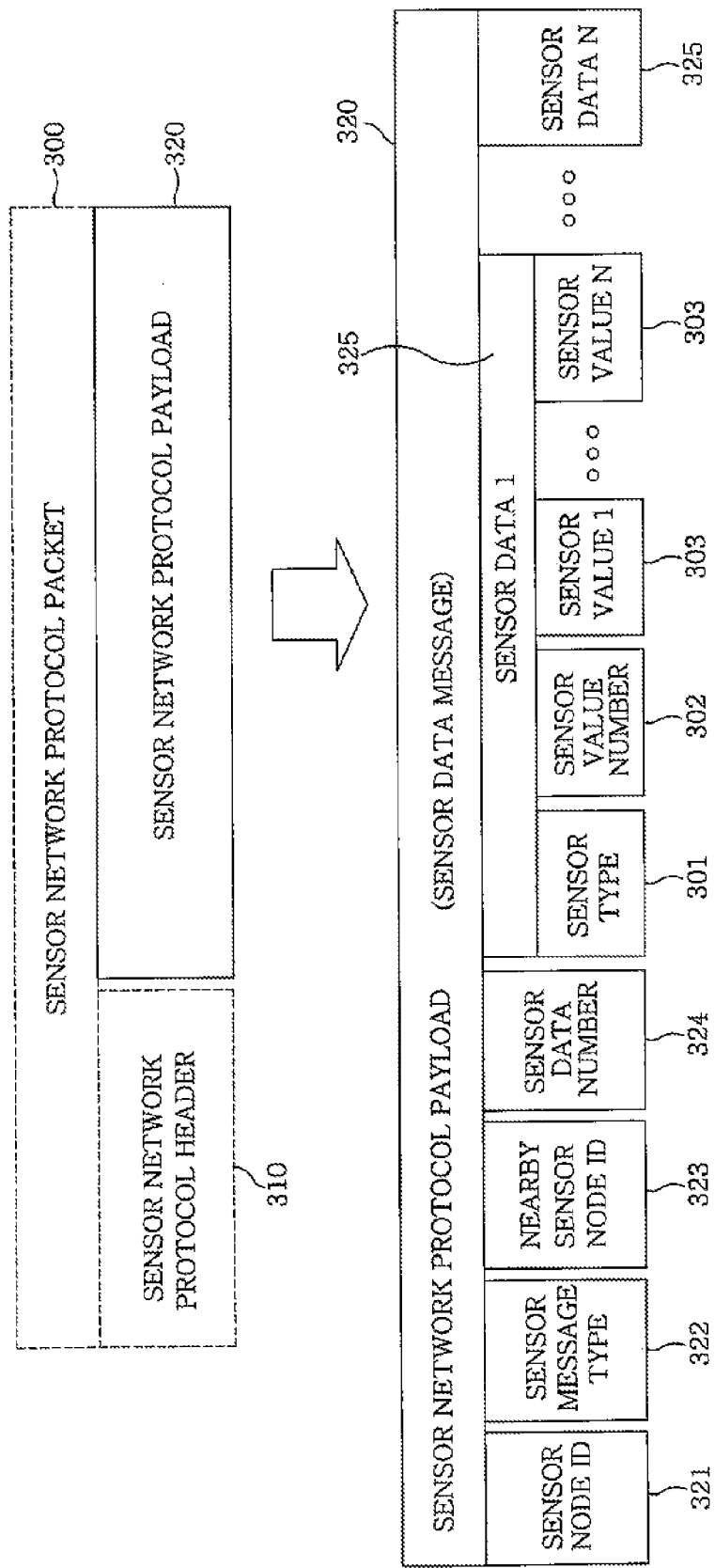
FIG. 5 illustrates a configuration of a sensor network protocol packet format for use in transmission of biological signal data in the user interface system in accordance with the present invention.

FIG. 5 illustrates a configuration of a sensor network protocol packet format for use in transmission of biological signal data in the user interface system in accordance with the present invention.

Referring to FIG. 5, the sensor network protocol packet 300 includes a sensor network protocol header 310 and a sensor network protocol payload 320. The sensor network protocol payload 320 has: a sensor node ID field 321 indicating a unique ID of a sensor node that transmits current sensor data; a sensor message type field 322 indicating a current sensor data message type (e.g., a control message or a data message); a nearby sensor node ID field 323 indicating a unique ID of a nearby sensor node with which the sensor node that transmits the current sensor data is connected; a sensor data number field 324 indicating the number of sensor data included in the current sensor data message; and sensor data fields 325 containing actually sensed data, wherein the number of the sensor data fields 325 is identical to that of sensor data. Each of the sensor data fields 325 includes: a sensor type field 301 indicating a type of a sensor (e.g., an acceleration, an angular speed, a pulse, a blood pressure, or a body temperature sensor) that produces the sensor data included in the sensor data fields 325; a sensor value number field 302 indicating the number of sensor values included in the sensor data; and sensor value fields 303 including sensed data values, wherein the number of the sensor value fields 303 corresponds to the value of the sensor value number field 302.

The reason for transmitting several sensor values for one sensor is to avoid a loss of the sensed data values during a transmission interval $I_t$ when the transmission interval $I_t$ is greater than a sensing interval $I_s$ of a sensor ($I_t > I_s$). In addition to the above-described basic fields, the sensor network protocol payload 320 may include fields having a variety of message information suitable for applications.

FIG. 6 illustrates a configuration of a sensor map database for use in the user interface system in accordance with the present invention. The sensor map database (DB) 400 is configured so that the user location management unit 205 of the service apparatus 141, 142 or 143 can retrieve a name of a space where a corresponding sensor node is installed and coordinate information of location of the corresponding sensor node by using the nearby sensor node ID field 323 as a key.

Referring to FIG. 6, the sensor map DB 400 includes: a sensor node ID field 401 used as a database retrieval key; a sensor space name field 402 for storing a space name (e.g., an inner room, a living room, a garden) suitably defined for a service environment; and a sensor coordinate field 403 for storing a coordinate of the sensor node in a 2-dimensional or 3-dimensional coordinate system. In addition to the above-described basic fields, the sensor map DB 400 may include fields having a variety of message information suitable for applications.

From the sensor map DB 400, the user location management unit 205 retrieves the current location information of the user 1 based on the nearby sensor node ID 323 in the biological signal data.

FIGS. 7A to 7D illustrate an embodiment of a mobility support procedure for the biological signal sensor apparatus 110, which is a mobile wireless sensor node, or the wireless sink node 130 mounted on the intelligent robot 143 in the user interface system in accordance with the present invention. This embodiment is based on a tree topology in a sensor network, in which a mobile wireless sensor node or a wireless sink node is a leaf node and stationary wireless nodes in a service space serve as router nodes. The mobility support procedure in such a sensor network is a kind of handover protocol to seamlessly keep the connection between the sensor network and a node moving in the service space, i.e., the biological signal sensor apparatus 110 or the wireless sink node 130 mounted on the intelligent robot 143.

(S11)

Figure 7A:
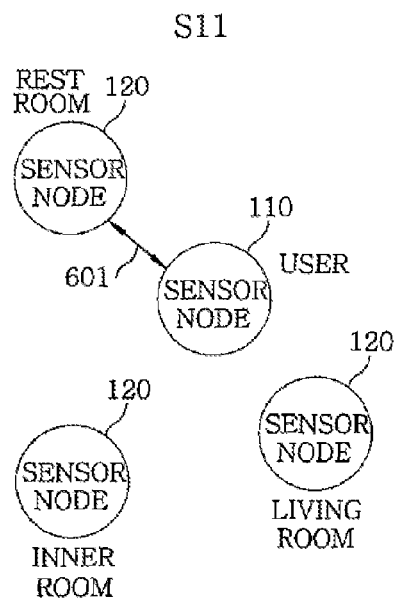
FIGS. 7A to 7D illustrate an embodiment of mobility support procedure for a wireless sensor node in the user interface system in accordance with the present invention.

It is assumed that a biological signal sensor apparatus 110 currently worn on a wrist of a user holds a connection 601 with a sensor network via a stationary wireless sensor node 120 installed in a rest room (i.e., the user is currently located in the rest room) (see, FIG. 7A).

(S12)

Figure 7B:
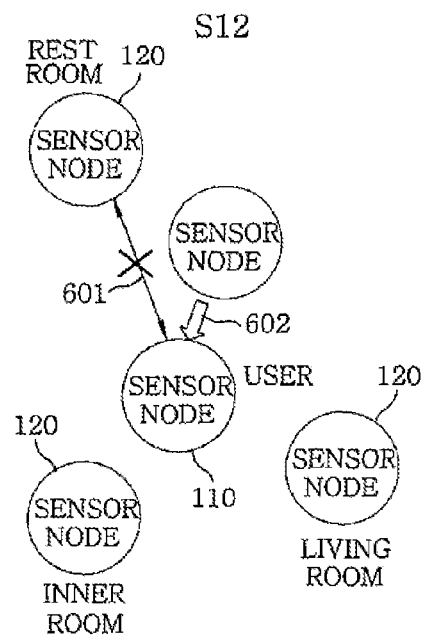

If the user conducts a movement 602 to enter the inner room which is out of a radio coverage of the stationary wireless sensor node 120 installed in the rest room, the connection 601 is made to be interrupted (i.e., the user-worn sensor node is disconnected from the sensor network) (see, FIG. 7B).

(S13)

Figure 7C:
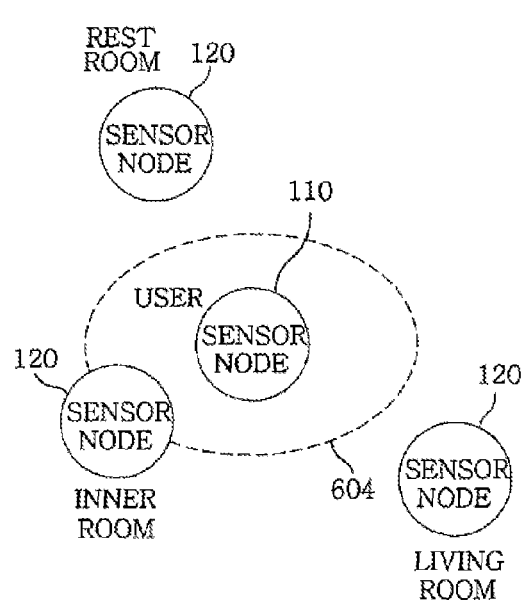

The biological signal sensor apparatus 110 detecting the disconnection searches for a stationary wireless sensor node 120 of which radio coverage 604 the user is located in (see, FIG. 7C).

(S14)

Figure 7D:
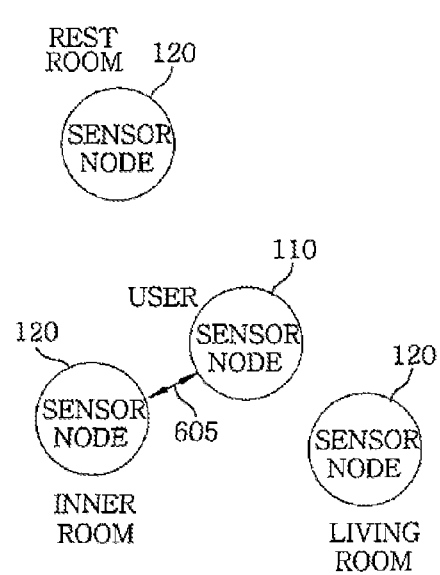

The biological signal sensor apparatus 110 creates a connection 605 with the searched stationary wireless sensor node 120 in the inner room, which is a nearby wireless sensor node (see, FIG. 7D).

The ID of the searched sensor node is a key for use in finding a space where the user is currently located. The ID is transmitted within the nearby sensor node ID field 323 of the above-described sensor network protocol packet 300, and, is used by the user location management unit 205 to retrieve the sensor map DB 400 of FIG. 6.

FIGS. 8A to 8D illustrate an embodiment of a mobility support procedure for the biological signal sensor apparatus 110, which is a mobile wireless sensor node, or the wireless sink node 130 mounted on the intelligent robot 143 in the user interface system in accordance with the present invention. This embodiment is based on the same tree topology in a sensor network as of FIGS. 7A to 7D, in which a mobile wireless sensor node or a wireless sink node is a leaf node and stationary wireless nodes in a service space serve as router nodes.

(S21)

The biological signal sensor apparatus 110 currently worn on a wrist of a user periodically receives Hello messages 701 from all stationary wireless sensor nodes 120 installed in a service environment around the user. The Hello messages 701 serve as RSSIs (received signal strength indicator) to find the most nearby stationary wireless sensor node 120 (see, FIG. 8A).

(S22)

Figure 8A:
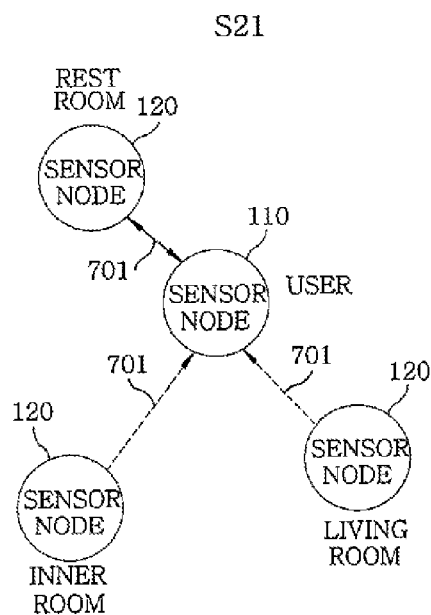
FIGS. 8A to 8D illustrate another embodiment of mobility support procedure for a wireless sensor node in the user interface system in accordance with the present invention.
Figure 8B:
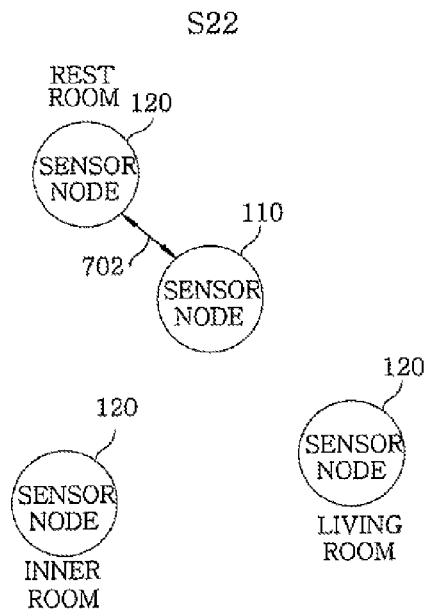

The biological signal sensor apparatus 110 creates and manages a nearby node table 800 of FIG. 9 based on the received Hello messages 701, and creates a connection 702 with a stationary wireless sensor node 120 having the highest wireless signal strength (i.e., a stationary wireless sensor node 120 at the nearest location) (see, FIG. 8B).

FIG. 9 illustrates a configuration view of an embodiment of the nearby node table 800 for use in the mobility support procedure for a wireless sensor node in the user interface system in accordance with the present invention. Referring to FIG. 9, the nearby node table 800 includes: a sensor node ID field 801 storing IDs of nearby stationary wireless sensor nodes 120; a wireless signal strength field 802 storing received signal strength of the respective stationary wireless sensor nodes 120; and a time stamp field 803 storing a time when a corresponding sensor node entry is created or lastly modified, wherein the time is used in searching for a sensor node entry which has not been updated for a specific period of time and deleting the sensor node entry from the nearby node table 800. In addition to the above-described basic fields, the nearby node table 800 may include fields having a variety of nearby node information suitable for applications.

(S23)

Figure 8C:
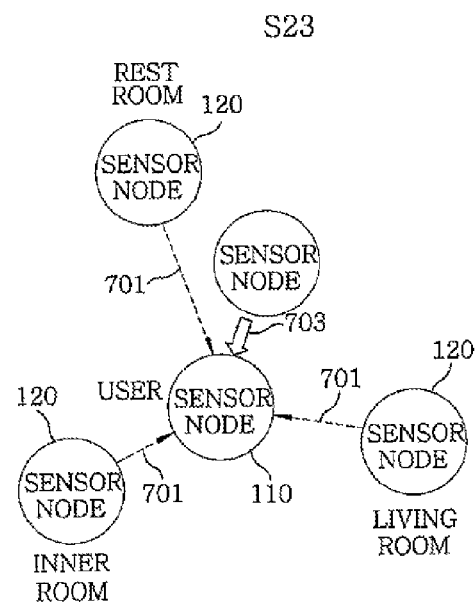

Even if the user conducts a movement 703 to enter an inner room, the biological signal sensor apparatus 110 continues to receive the Hello messages 701 from all stationary wireless sensor nodes 120 around the user (see, FIG. 8C).

(S24)

Figure 8D:
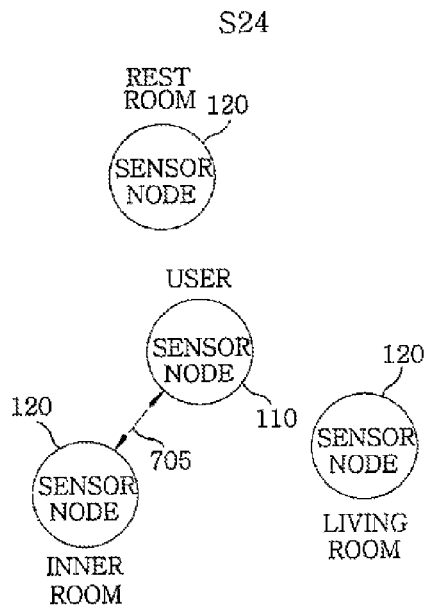

After the user has conducted the movement 703, the biological signal sensor apparatus 110 selects a stationary wireless sensor node 120 having the highest wireless signal strength (i.e., a stationary wireless sensor node 120 at the nearest location) based on the Hello messages 701 and creates a connection 705 with the selected stationary wireless sensor node 120 (see, FIG. 8D).

Hereinafter, exemplary embodiments of the user interface system in accordance with the present invention will be described with reference to FIGS. 10 to 14. The exemplary embodiments include a childcare service, an eldercare/infantcare service, a game/education service, a ubiquitous healthcare service, and an electrical device remote control service. These services may be separately provided by independent systems, respectively, or, two or more of these services may be provided as a combined service by a single integrated system.

Figure 10:
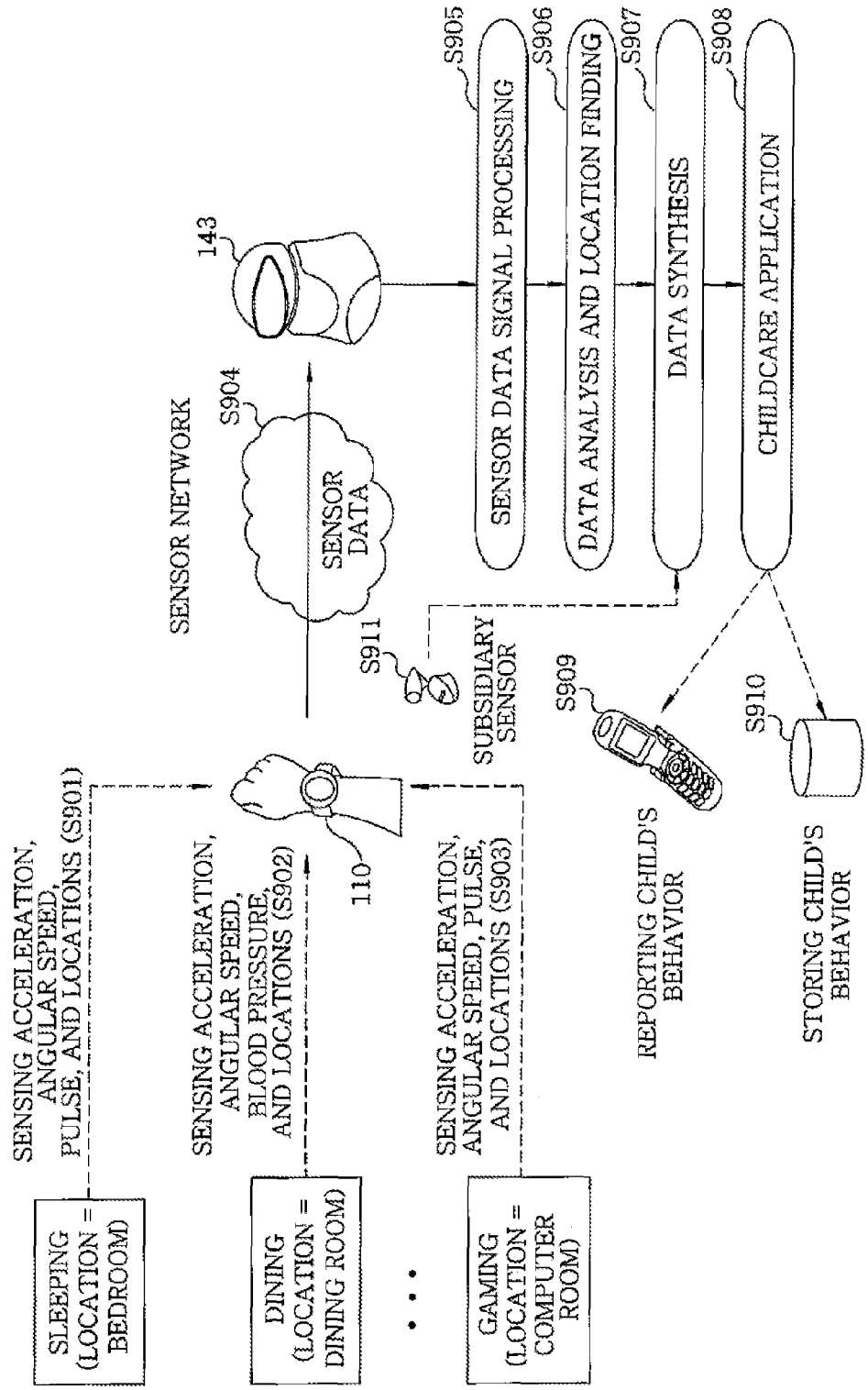
FIG. 10 illustrates an exemplary view of the user interface system using a biological signal sensor apparatus to provide a childcare service.

FIG. 10 illustrates an exemplary view of the user interface system using a biological signal sensor apparatus to provide a childcare service.

Referring to FIG. 10, the childcare service refers to a service in which, a biological signal sensor apparatus 110 senses behaviors of a child and a service apparatus such as an intelligent robot 143 or a home server 142 monitors and analyzes the behaviors via a sensor network to record the result or report the same to a guardian of the child in real time.

First, the child wears the biological signal sensor apparatus 110, and, then, the biological signal sensor apparatus 110 senses data such as an acceleration, an angular speed, a pulse, a blood pressure, a location (a bedroom, a dining room, a computer room, etc.) and the like (steps S901 to 903). These data are required to recognize the behaviors (sleeping, dinning, gaming, and other various behaviors) of the child to be cared. The sensed data is transmitted to the intelligent robot 143 via the sensor network (step S904).

The intelligent robot 143 performs pre-processing on the received sensor data through sensor data signal processing (step S905), and, then, recognizes meaning of the behaviors by performing sensor data analysis on the pre-processed sensor data and finds out a current location of the child wearing the sensor through location finding (step S906). The intelligent robot 143 synthesizes the analyzed sensor data and the location data to finally recognize the meaning of the behaviors (step S907), and provides the childcare service through childcare applications (step S908). To be specific, the intelligent robot 143 reports the behaviors to the guardian in real time (step S909), or stores the same in a database (step S910).

Further, if a subsidiary visual sensor is mounted on the intelligent robot 143 as a subsidiary sensor, the intelligent robot 143 is made to move to a current user location and create subsidiary data such as user pose data through processing image obtained via the subsidiary sensor (step S911). By using the subsidiary data in the data synthesis, the intelligent robot 143 can recognize the behaviors more accurately. In order to provide more intelligent and effective services, the intelligent robot 143 may automatically output, using a voice output device or a speaker mounted thereon, a speech to control or restrict behaviors of the child, or may allow the guardian to have a conversation with the child in real time.

Figure 11:
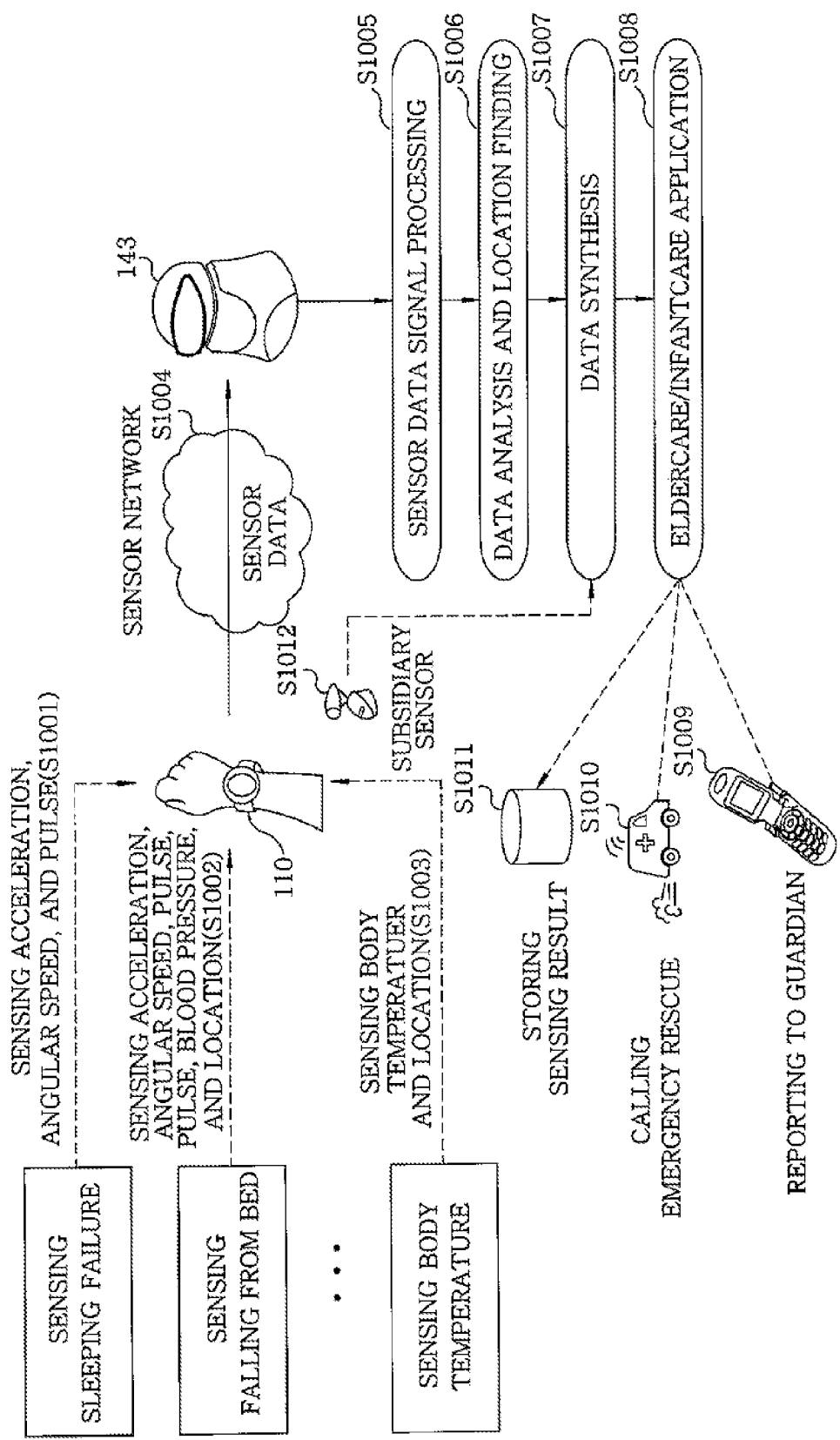
FIG. 11 illustrates an exemplary view of the user interface system using a biological signal sensor apparatus to provide an eldercare/infantcare service.

FIG. 11 illustrates an exemplary view of the user interface system using a biological signal sensor apparatus to provide an eldercare/infantcare service.

Referring to FIG. 11, the eldercare/infantcare service refers to a service in which, a biological signal sensor apparatus 110 senses states of an elder or an infant who cannot freely move or talk, and a service apparatus such as an intelligent robot 143 or a home server 142 monitors and analyzes the states via a sensor network to record the result, report the same to a guardian thereof in real time, or call emergency rescue.

First, the elder or the infant wears the biological signal sensor apparatus 110, and, then, the biological signal sensor apparatus 110 senses data such as an acceleration, an angular speed, a pulse, a blood pressure, a body temperature, a location and the like (steps S1001 to 1003). These data are required to recognize the states (movements while sleeping, falling from a bed, a body temperature of an infant, and other various states) to be observed. The sensed data is transmitted to the intelligent robot 143 via the sensor network (step S1004).

The intelligent robot 143 performs pre-processing on the received sensor data through sensor data signal processing (step S1005), and, then, recognizes meaning of the states by performing sensor data analysis on the pre-processed sensor data and finds out a current location of the elder/infant wearing the sensor through location finding (step S1006). The intelligent robot 143 synthesizes the analyzed sensor data and the location data to finally recognize the meaning of the states (step S1007), and provides the eldercare/infantcare service through eldercare/infantcare applications (step S1008). To be specific, the intelligent robot 143 reports the states to the guardian in real time (step S1009), calls emergency rescue (step S1010), or stores the states in a database (step S1011).

Further, if a subsidiary visual sensor is mounted on the intelligent robot 143 as a subsidiary sensor, the intelligent robot 143 is made to move to a current user location and create subsidiary data such as user pose data through processing image obtained via the subsidiary sensor (step S1012). By using the subsidiary data in the data synthesis, the intelligent robot 143 can recognize the states more accurately. In order to provide more intelligent and effective services, the intelligent robot 143 may automatically output, using a voice output device or a speaker mounted thereon, a speech to relieve the user, or may allow the user to have a conversation with the guardian or emergency rescuer in real time.

Figure 12:
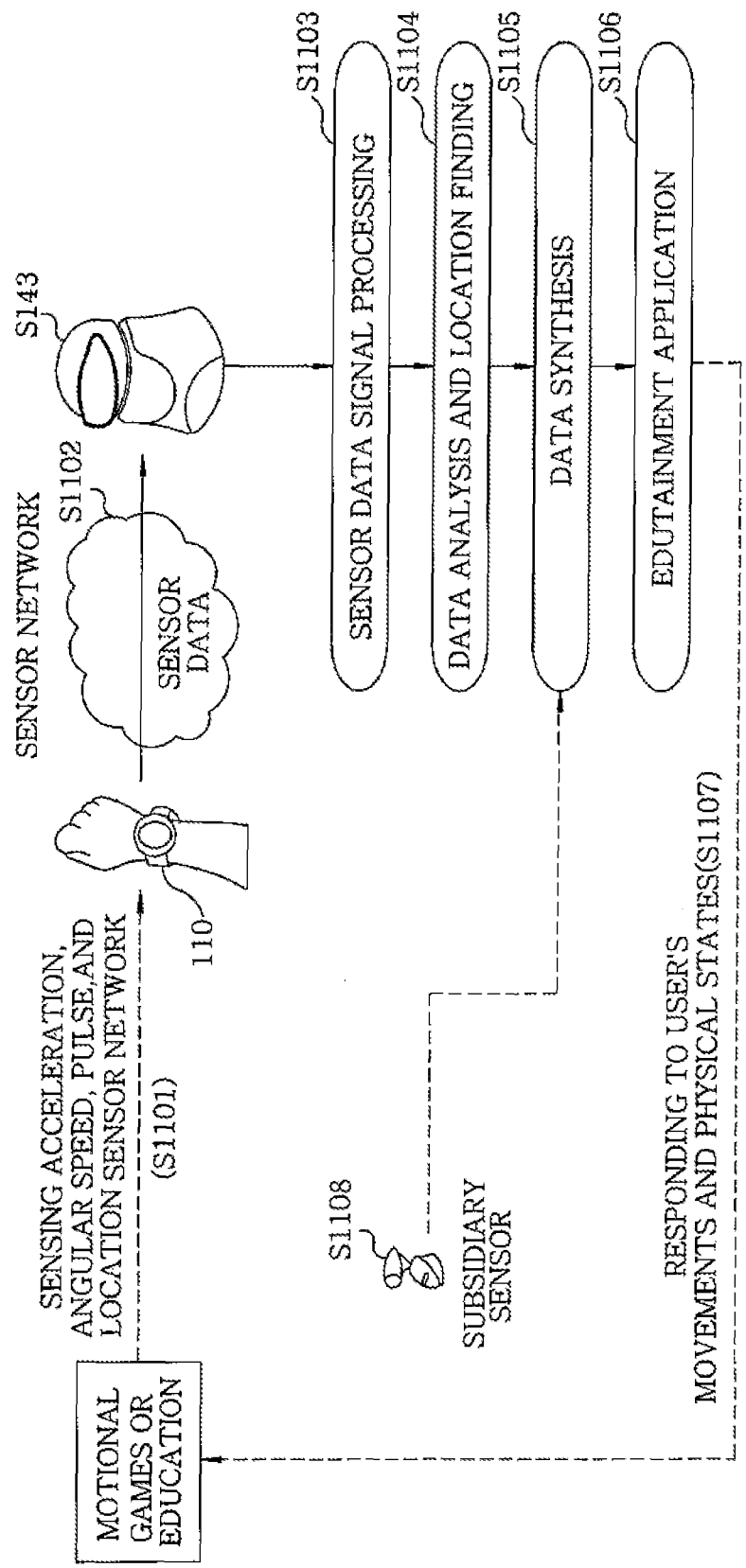
FIG. 12 illustrates an exemplary view of the user interface system using a biological signal sensor apparatus to provide a game/education service.

FIG. 12 illustrates an exemplary view of the user interface system using a biological signal sensor apparatus to provide a game/education service.

Referring to FIG. 12, a user interface of the game/education service is not a joystick, other existing game interface, or a general user interface device such as a mouse or a keyboard. Instead, a biological signal sensor apparatus 110 senses movements of hands of a user and changes of physical states of the user. The biological signal sensor apparatus 110 transmits sensor data to a service apparatus such as a computer, an intelligent robot or a home server, and the service apparatus analyzes the sensor data to provide a variety of games, educational application programs and content, and the like.

First, a child, who is a user of the game/education service, wears the biological signal sensor apparatus 110, and, then, the biological signal sensor apparatus 110 senses data such as an acceleration, an angular speed, a pulse, a location and the like (steps S1101). These data are required to recognize behaviors and states of the user to provide games, educational application programs and content, and the like. The sensed data is transmitted to an intelligent robot 143, for example, via the sensor network (step S1102).

The intelligent robot 143 performs pre-processing on the received sensor data through sensor data signal processing (step S1103), and, then, recognizes the behaviors and the states of the user by performing sensor data analysis on the pre-processed sensor data and finds out a current location of the user wearing the sensor through location finding (step S1104). The intelligent robot 143 synthesizes the analyzed sensor data and the location data to finally recognize the meaning of the behaviors and the states of the user (step S1105), and provides the game/education service through game/education applications (step S1106).

In such a game/education service, movements data of the user obtained by, e.g., an acceleration sensor and an angular speed sensor is used as a means for replacing an user input device in the game or education, and physical state data of the user obtained by, e.g., a pulse sensor is used to detect changes of the physical states of the user under the game/education service. For example, in a game service, a pulse of a user playing the game for a certain period of time is monitored via the sensor network to measure a fatigue or excitement level of the user and responses thereto are made in an intelligent manner (step S1107), thereby providing more excellent game service. Further, the user location data can be used for automatic termination of the game or education when the user moves to other space, or can be used for a location-based game such as a hide-and-seek game with the intelligent robot 143 which is a movable service apparatus.

Further, if a subsidiary visual sensor is mounted on the intelligent robot 143 as a subsidiary sensor, the intelligent robot 143 is made to create subsidiary data such as user pose data or a color or shape data of item used in the game or education through processing image obtained via the subsidiary sensor (step S1108). By using the subsidiary data in the data synthesis, the intelligent robot 143 can recognize the user input more accurately, thereby providing more intelligent and effective services.

Figure 13:
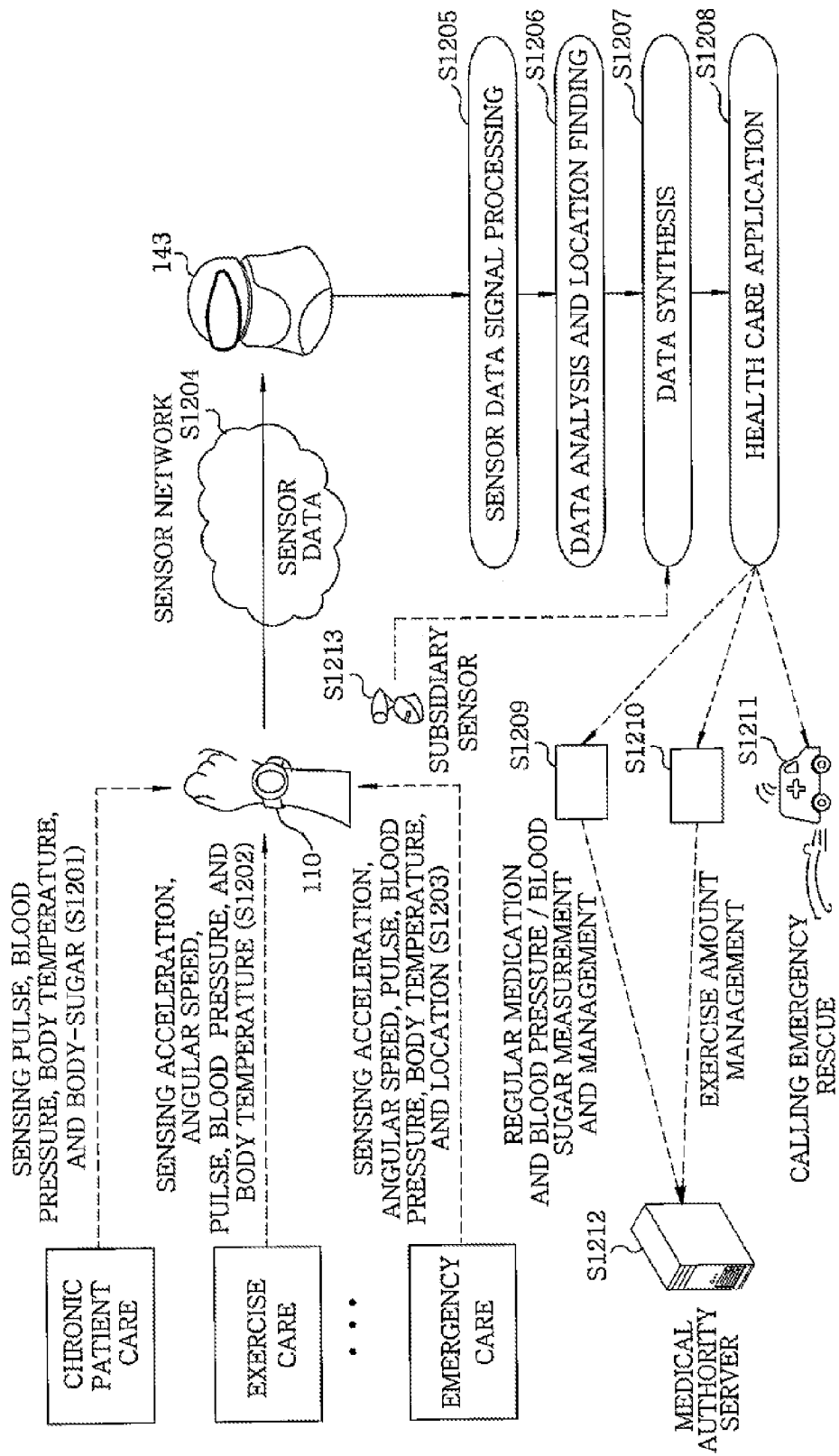
FIG. 13 illustrates an exemplary view of the user interface system using a biological signal sensor apparatus to provide a ubiquitous healthcare service.

FIG. 13 illustrates an exemplary view of the user interface system using a biological signal sensor apparatus to provide a ubiquitous healthcare service.

Referring to FIG. 13, the ubiquitous healthcare service is a service in which, a biological signal sensor apparatus 110 senses ordinary physical states of a chronic patient, physical states while exercising, physical states in an emergency situation, and the like, and a service apparatus such as an intelligent robot 143 or a home server 142 monitors and analyzes the states via a sensor network to, perform a regular medication, a blood pressure/blood sugar measurement, an exercise amount management, or an emergency rescue call when necessary.

First, a user (a chronic patient or a night worker) for whom the healthcare service is needed wears the biological signal sensor apparatus 110, and, then, the biological signal sensor apparatus 110 senses data such as a pulse, a blood pressure, a body temperature, a blood sugar, an acceleration, an angular speed, a blood pressure, a location and the like (steps S1201 to 1203). These data are necessary for chronic disease care, exercise amount care, or emergency care such as a blackout or a heat attack. The sensed data is transmitted to the intelligent robot 143 via the sensor network (step S1204).

The intelligent robot 143 performs pre-processing on the received sensor data through sensor data signal processing (step S1205), and, then, recognizes meaning of the states by performing sensor data analysis on the pre-processed sensor data and finds out a current location of the user wearing the sensor through location finding (step S1206). The intelligent robot 143 synthesizes the analyzed sensor data and the location data to finally recognize the meaning of the states (step S1207), and provides the healthcare service through healthcare applications (step S1208). To be specific, the intelligent robot 143 performs a regular medication and a blood pressure/blood sugar measurement (step S1209), manages exercise amount (step S1210), or calls emergency rescue (step S1211) when necessary.

In particular, records for the regular medication, blood pressure/blood-sugar measurement, and ordinary exercise amount are recorded in a server in a medical authority which provides medical services to the user and utilized as data for medical treatment (step S1212).

Further, if a subsidiary visual sensor is mounted on the intelligent robot 143 as a subsidiary sensor, the intelligent robot 143 is made to move to a current user location and create subsidiary data such as user pose data through processing image obtained via the subsidiary sensor (step S1213). By using the subsidiary data in the data synthesis, the intelligent robot 143 can recognize the states more accurately. In order to provide more intelligent and effective services, the intelligent robot 143 may regularly notify, using a voice output device or a speaker mounted thereon, a medication time or a blood pressure/blood sugar measurement time, or may inform advice on exercise amount or emergency measures to be taken by the user in an emergency situation. Further, the intelligent robot 143 may allow the user to have a conversation with an emergency rescuer in real time.

FIG. 14 illustrates an exemplary view of the user interface system using a biological signal sensor apparatus to provide an electrical device remote control service.

Referring to FIG. 14, a user interface of the electrical device remote control service is not a remote controller using buttons or a joystick. Instead, a biological signal sensor apparatus 110 senses movements of hands of a user. The biological signal sensor apparatus 110 transmits sensor data to a service apparatus such as a computer 141, a home server 142, or an intelligent robot 143, and the service apparatus remotely controls electrical devices in service spaces.

First, the user wears the biological signal sensor apparatus 110, and, then, the biological signal sensor apparatus 110 senses data such as an acceleration, an angular speed, a location and the like (steps S1301). The data are required to recognize behaviors of the user to remotely control an electrical device, e.g., the intelligent robot 143. The sensed data is transmitted to the intelligent robot 143, which is a control object, via the sensor network (step S1302).

The intelligent robot 143 performs pre-processing on the received sensor data through sensor data signal processing (step S1303), and, then, recognizes the behaviors conducted by the user for remote control by performing sensor data analysis on the pre-processed sensor data and finds out a current location of the user wearing the sensor through location finding (step S1304). The intelligent robot 143 synthesizes the analyzed sensor data and the location data to finally recognize control commands (step S1305), and is remotely controlled through electrical device control applications (step S1306).

Further, if a subsidiary visual sensor is mounted on the intelligent robot 143 as a subsidiary sensor, the intelligent robot 143 is made to create subsidiary data such as user pose data through processing image obtained via the subsidiary sensor (step S1307). By using the subsidiary data in the data synthesis, the intelligent robot 143 can recognize the control commands from the user more accurately, so that more intelligent and effective remote control services can be provided.

While the invention has been shown and described with respect to the embodiments, it will be understood by those skilled in the art that various changes and modification may be made without departing from the scope of the invention as defined in the following claims.

What is claimed is:

1. A user interface system, comprising:
a biological signal sensor apparatus, worn on a user's body and serving as a mobile wireless sensor node in a wireless sensor network, for sensing biological signals of a user to generate biological signal data;
a plurality of stationary wireless sensor nodes, installed in living spaces of the user, for performing wireless communications with the biological signal sensor apparatus;
a plurality of wireless sink nodes wirelessly connected with the stationary wireless sensor nodes to form the wireless sensor network;
a service unit for processing the biological signal data transmitted via the wireless sink nodes to provide to the user application services based on location information of the user who stays in any one of the living spaces in the wireless sensor network, wherein the service unit includes:
a sink node connection unit;
a sink node application program interface unit for providing basic libraries to support communications with the wireless sink nodes;
a sensor signal processing unit for performing pre-processing on the biological signal data received from the wireless sink nodes;
a sensor data analysis unit for analyzing patterns of the pre-processed biological signal data by applying a learning or recognizing algorithm thereto;
a user location management unit for obtaining the location information of the user based on the biological signal data received from the wireless sink nodes;
an application service unit for providing the application services to the user based on the analyzed biological signal data and the location information of the user; and
a sensor map DB (database) from which a space name of a space where a sensor node is installed and a coordinate of a location of the sensor node are retrieved by using a sensor node ID of the sensor node as a key, and the user location management unit obtains the location information of the user by retrieving the sensor map DB using the sensor node ID of the nearby sensor node; and
wherein if the biological signal sensor apparatus, which has been connected with the wireless sensor network via the stationary wireless sensor node among the stationary wireless sensor nodes, goes out of a radio coverage of the stationary wireless sensor node, the biological signal sensor apparatus searches for another stationary wireless sensor node having a radio coverage within which the user is located and creates a new connection therewith.

2. The user interface system of claim 1, further comprising:
a service server, connected with the service unit via an external communications network, for providing to the user the application services based on the biological signal data via the service unit,
wherein the service unit further includes a server interoperation unit for providing interoperability with the service server.

3. The user interface system of claim 1, further comprising:
a subsidiary sensor apparatus for obtaining image data of the user to assist the biological signal sensor apparatus,
wherein the service unit further includes a sensor data synthesis unit for combining the analyzed biological signal data and the image data obtained by the subsidiary sensor apparatus to extract meaningful context therefrom and transmitting the meaningful context to the application service unit to provide the application services.

4. The user interface system of claim 1, wherein the service unit includes a service apparatus, connected with the wireless sink nodes, the service apparatus providing the application services via application programs stored thereon.

5. The user interface system of claim 1, wherein the service unit includes:
a service apparatus connected with the wireless sink nodes; and
a host apparatus, connected with the service apparatus, for providing the application services via application programs embedded therein.

6. The user interface system of claim 1, wherein the biological signal sensor apparatus sets the nearby sensor node ID field of a sensor network protocol payload to be transmitted as the sensor node ID of the stationary wireless sensor node with which the new connection is created.

7. The user interface system of claim 1, wherein the biological signal sensor node measures signal strength of a message received from each of the stationary wireless sensor nodes and creates a connection with the stationary wireless sensor node which transmits the message having the highest signal strength.

8. The user interface system of claim 7, wherein the biological signal sensor node creates and manages a nearby node table based on the measured signal strength.

9. A user interface system, comprising:
a biological signal sensor apparatus, worn on a user's body and serving as a mobile wireless sensor node in a wireless sensor network, for sensing biological signals of a user to generate biological signal data;
a plurality of stationary wireless sensor nodes, installed in living spaces of the user, for performing wireless communications with the biological signal sensor apparatus;
a plurality of wireless sink nodes wirelessly connected with the stationary wireless sensor nodes to form the wireless sensor network;
a service unit for processing the biological signal data transmitted via the wireless sink nodes to provide to the user application services based on location information of the user who stays in any one of the living spaces in the wireless sensor network;
wherein the service unit includes:
a sink node connection unit;
a sink node application program interface unit for providing basic libraries to support communications with the wireless sink nodes;
a sensor signal processing unit for performing pre-processing on the biological signal data received from the wireless sink nodes;
a sensor data analysis unit for analyzing patterns of the pre-processed biological signal data by applying a learning or recognizing algorithm thereto;
a user location management unit for obtaining the location information of the user based on the biological signal data received from the wireless sink nodes;

an application service unit for providing the application services to the user based on the analyzed biological signal data and the location information of the user; and a sensor map DB (database) from which a space name of a space where a sensor node is installed and a coordinate of a location of the sensor node are retrieved using a sensor node ID of the sensor node as a key, and the user location management unit obtains the location information of the user by retrieving the sensor map DB using the sensor node ID of the nearby sensor node, wherein the biological signal sensor node measures signal strength of a message received from each of the stationary wireless sensor nodes and creates a connection with the stationary wireless sensor node which transmits a message having the highest signal strength, and the biological signal sensor node creates and manages a nearby node table based on the measured signal strength, and wherein the nearby node table includes:

a sensor node ID field storing the sensor node ID of each of the stationary wireless sensor nodes located around the user; and a wireless signal strength field for storing the signal strength for each of the stationary wireless sensor nodes.

10. The user interface system of claim 9, wherein the nearby node table further includes a time stamp field for storing a time when a corresponding sensor node entry is created or lastly modified, wherein the time is used in searching for a sensor node entry which has not been updated for a specific period of time and deleting the sensor node entry from the nearby node table.

* * * * *